(12) United States Patent
Chermak

(10) Patent No.: US 11,103,212 B2
(45) Date of Patent: Aug. 31, 2021

(54) SYSTEMS AND METHODS FOR ASSOCIATING AND VERIFYING AN ASSOCIATION OF A TRANSDUCER WITH AN IMAGING DEVICE

(71) Applicant: KONINKLIJKE PHILIPS N.V., Eindhoven (NL)

(72) Inventor: Dale Allen Chermak, Bothell, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 194 days.

(21) Appl. No.: 15/772,973

(22) PCT Filed: Oct. 18, 2016

(86) PCT No.: PCT/IB2016/056243
§ 371 (c)(1),
(2) Date: May 2, 2018

(87) PCT Pub. No.: WO2017/081566
PCT Pub. Date: May 18, 2017

(65) Prior Publication Data
US 2018/0317882 A1    Nov. 8, 2018

Related U.S. Application Data

(60) Provisional application No. 62/253,716, filed on Nov. 11, 2015.

(51) Int. Cl.
*H04L 29/00* (2006.01)
*A61B 8/00* (2006.01)
(Continued)

(52) U.S. Cl.
CPC .............. *A61B 8/4438* (2013.01); *A61B 8/56* (2013.01); *A61B 8/565* (2013.01); *G16H 30/20* (2018.01); *G16H 30/40* (2018.01); *G16H 40/63* (2018.01)

(58) Field of Classification Search
CPC ........ A61B 8/4438; A61B 8/56; G16H 40/63; G16H 30/20; G06F 21/30; G06F 21/44; G06F 21/70; H04L 63/08; H04L 63/10
See application file for complete search history.

(56) References Cited

U.S. PATENT DOCUMENTS

2004/0171935 A1\* 9/2004 Van Creveld ......... G01S 15/899
600/437
2009/0034677 A1\* 2/2009 Prestidge ............... G01B 5/012
377/2

(Continued)

FOREIGN PATENT DOCUMENTS

JP    2006345964 A    12/2006

*Primary Examiner* — Jeffrey C Pwu
*Assistant Examiner* — Helai Salehi

(57) ABSTRACT

The present disclosure describes system, application, and/or methods for enabling operation of a transducer probe with a medical imaging device. An example method includes the steps of retrieving a user identification code assigned to a user associated with an imaging device, retrieving a transducer identification code of a transducer probe from a memory of the transducer probe responsive to connecting the transducer probe to the imaging device, generating a temporary digital key based on the user identification code and the transducer identification code, retrieving a stored digital key from the memory of the transducer probe, verifying an association of the transducer probe including comparing the stored digital key with the temporary digital key, enabling operation of the transducer probe with the imaging device if the stored digital key matches the temporary digital key.

18 Claims, 7 Drawing Sheets

(51) Int. Cl.
    *G16H 40/63*     (2018.01)
    *G16H 30/40*     (2018.01)
    *G16H 30/20*     (2018.01)

(56) References Cited

U.S. PATENT DOCUMENTS

| | | | |
|---|---|---|---|
| 2009/0070585 A1* | 3/2009 | Prestidge | G06F 21/44 713/168 |
| 2010/0191121 A1 | 7/2010 | Satoh et al. | |
| 2013/0158397 A1* | 6/2013 | K. | G16H 10/60 600/437 |
| 2015/0032004 A1 | 1/2015 | Kim et al. | |

* cited by examiner

| Imaging device / Transducer probe | Imaging device 1 | Imaging device 2 | Imaging device 3 | Imaging device 4 | Imaging device 5 |
|---|---|---|---|---|---|
| Transducer 1 / Key-type 1 — 124-a | ✓ | ✓ | ✓ | ✓ | ✗ |
| Transducer 2 / Key-type 1 — 124-b | ✗ | ✗ | ✗ | ✗ | ✓ |
| Transducer 3 / Key-type 2 — 124-c | ✓ | ✓ | ✗ | ✗ | ✗ |
| Key-type 2 — 124-d | | | | | |

{ Imaging device 1 – Imaging device 4 }: User 1
{ Imaging device 5 }: User 2

FIG. 5

SYSTEMS AND METHODS FOR ASSOCIATING AND VERIFYING AN ASSOCIATION OF A TRANSDUCER WITH AN IMAGING DEVICE

This application is the U.S. National Phase application under 35 U.S.C. § 371 of International Application No. PCT/IB2016/056243 filed on Oct. 18, 2016, which claims the benefit of Provisional Application Ser. No. 62/253,716, filed Nov. 11, 2015. These applications are hereby incorporated by reference herein.

BACKGROUND

The present disclosure relates generally to medical imaging systems. A typical imaging system, such as an ultrasound system, includes a transducer probe which is removably connected to an imaging device. This enables the use of different transducer probes with the same imaging device as well as use of the same transducer probe with different imaging devices. While this may be advantageous in some situations, the removable coupling between the transducer and imaging device may allow for the theft or unauthorized use of a transducer.

In particular, advancements in ultrasound imaging systems have reduced the size of transducer probes and/or cables used to connect the probes to the imaging device. In some modern digital imaging systems, significantly smaller and thinner cables may be used to connect a transducer probe, having typically smaller form factor, to the imaging device. The reduced size of the transducer probes and/or cables may increase the risk of theft or unauthorized use of a transducer. Additionally, newer ultrasound imaging systems may be configured such that the cable connecting the probe to the imaging device may be disconnected not only from the imaging device side but from the probe side as well, thus increasing the risk of theft of a transducer. Improved techniques for enhancing security and reducing the risk of theft of transducer probes may thus be desirable.

SUMMARY OF THE INVENTION

According to an illustrative embodiment of the invention, a method may include the steps of retrieving a user identification code assigned to a user associated with an imaging device, retrieving a transducer identification code of a transducer probe from a memory of the transducer probe responsive to coupling the transducer probe to the imaging device, generating a temporary digital key based on the user identification code and the transducer identification code, retrieving a stored digital key from the memory of the transducer probe, verifying an association of the transducer probe including comparing the stored digital key with the temporary digital key, and enabling operation of the transducer probe with the imaging device if the stored digital key matches the temporary digital key In some examples, the method may further include the steps of deleting the temporary digital key from the imaging device following the verifying step and/or deleting the temporary digital key from the imaging device when the transducer probe is disconnected form the imaging device, when the imaging device is powered down, or when execution of an imaging application on the imaging device is terminated. In some examples, the method may further include the step of generating an alert if the temporary digital key does not match the stored digital key.

In some examples, the method may further include the step of associating the transducer probe with the imaging device. The step of associating the transducer probe with the imaging device may include the steps of retrieving the user identification code from a remote server wirelessly coupled to the imaging device responsive to coupling the transducer probe to the imaging device, storing the user identification code in the memory of the imaging device, retrieving the transducer identification code of the transducer probe, generating the digital key based, at least in part, on the user identification code and the transducer identification code, and transmitting a digital key to the transducer probe to be stored in the memory of the transducer probe as the stored digital key. In some examples, the step of associating the transducer probe with the imaging device may further include the steps of transmitting a request for the transducer identification code to the remote server, the transmitting a request for the transducer identification code comprising transmitting a device identification code, a user identification code, or both to the remote server, receiving the transducer identification code from the remote server, and transmitting the transducer identification code to the transducer probe to be stored in the memory of the transducer probe.

In some examples, the step of associating the transducer probe with the imaging device may further include the steps of transmitting a request for the user identification code to the remote server, the transmitting a request for the user identification code including transmitting a device identification code to the remote server, retrieving the user identification code from the remote server, and storing the user identification code in a memory of the imaging device. In some examples, the step of associating the transducer probe with the imaging device may further include the steps of retrieving a device identification code associated with the imaging device from the memory of the imaging device responsive to coupling the first transducer to the imaging device, and generating the digital key based further on the device identification code retrieved from the memory of the imaging device. In some examples, the method may further include the step of storing the digital key, the temporary digital key, or both, only in volatile memory of the imaging device.

According to another illustrative embodiment of the invention, a medical imaging system may include an imaging device configured to be removably connected to a transducer probe, the imaging device having a user interface, a memory, and a processor coupled to the user interface and the memory, the memory including instructions for retrieving a user identification code assigned to a user associated with the imaging device, retrieving a transducer identification code of a transducer probe responsive to connecting the transducer probe to the imaging device, generating a temporary digital key based, in part, on the user identification code and the transducer identification code, retrieving a stored digital key from a memory of the transducer probe, verifying an association of the transducer probe with the imaging device, and enabling operation of the transducer probe with the imaging device if the stored digital key matches the temporary digital key.

In some examples, the imaging device further includes instructions for deleting the temporary digital key from the imaging device upon the occurrence of an event. In some examples, the imaging device further includes instructions for generating the digital key and transmitting the digital key to the transducer probe to be stored thereon as the stored digital key. In some examples, the imaging device is configured to store the temporary digital key, the digital key, or both, only in volatile memory of the imaging device. In some examples, the imaging device further includes instruction for generating an alert if the temporary digital key does not match the stored digital key. In some examples, the imaging device further includes instruction for generating the digital key based further on a device identification code of the imaging device.

In some examples, the system may further include the transducer probe, wherein the transducer probe may include a USB connector for coupling the transducer probe to the imaging device. In some example, the memory of the transducer probe may include a first stored digital key based on the user identification code, the transducer identification code, and a first imaging device identification code, and a second stored digital key based on the user identification code, the transducer identification code, and a second imaging device identification code. In some examples, the imaging device may further include instructions for comparing the temporary digital key with first stored digital key and if the temporary digital key does not match the first stored digital key, comparing the temporary digital key with the second stored digital key. In some examples, the system may further include a server and the imaging device may be wirelessly connected to the server. The imaging device may further include instructions for retrieving the user identification code from the server and storing the user identification code in the memory of the imaging device. In some examples, the imaging device may further include instruction for retrieving the transducer identification code from the server and transmitting the transducer identification number to the transducer probe to be stored in the memory of the transducer probe.

BRIEF DESCRIPTION OF THE DRAWINGS

FIG. 5 is a table showing association between a number of transducer probes and a number of imaging devices according to some embodiments of the present disclosure.

DETAILED DESCRIPTION OF PREFERRED EMBODIMENTS

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

In one embodiment there is provided a system, application, and/or method for enabling operation of a transducer probe with a medical imaging device. In some examples, the method may include the steps of retrieving a user identification code, e.g., a user identification number, assigned to a user associated with an imaging device, retrieving a transducer identification code of a transducer probe from a memory of the transducer probe responsive to connecting the transducer probe to the imaging device, generating a temporary digital key based on the user identification code and the transducer identification code, retrieving a stored digital key from the memory of the transducer probe, verifying an association of the transducer probe including comparing the stored digital key with the temporary digital key, enabling operation of the transducer probe with the imaging device if the stored digital key matches the temporary digital key. In some examples, the steps of methods described herein may be performed in different order or steps may be omitted or added.

Figure 1:
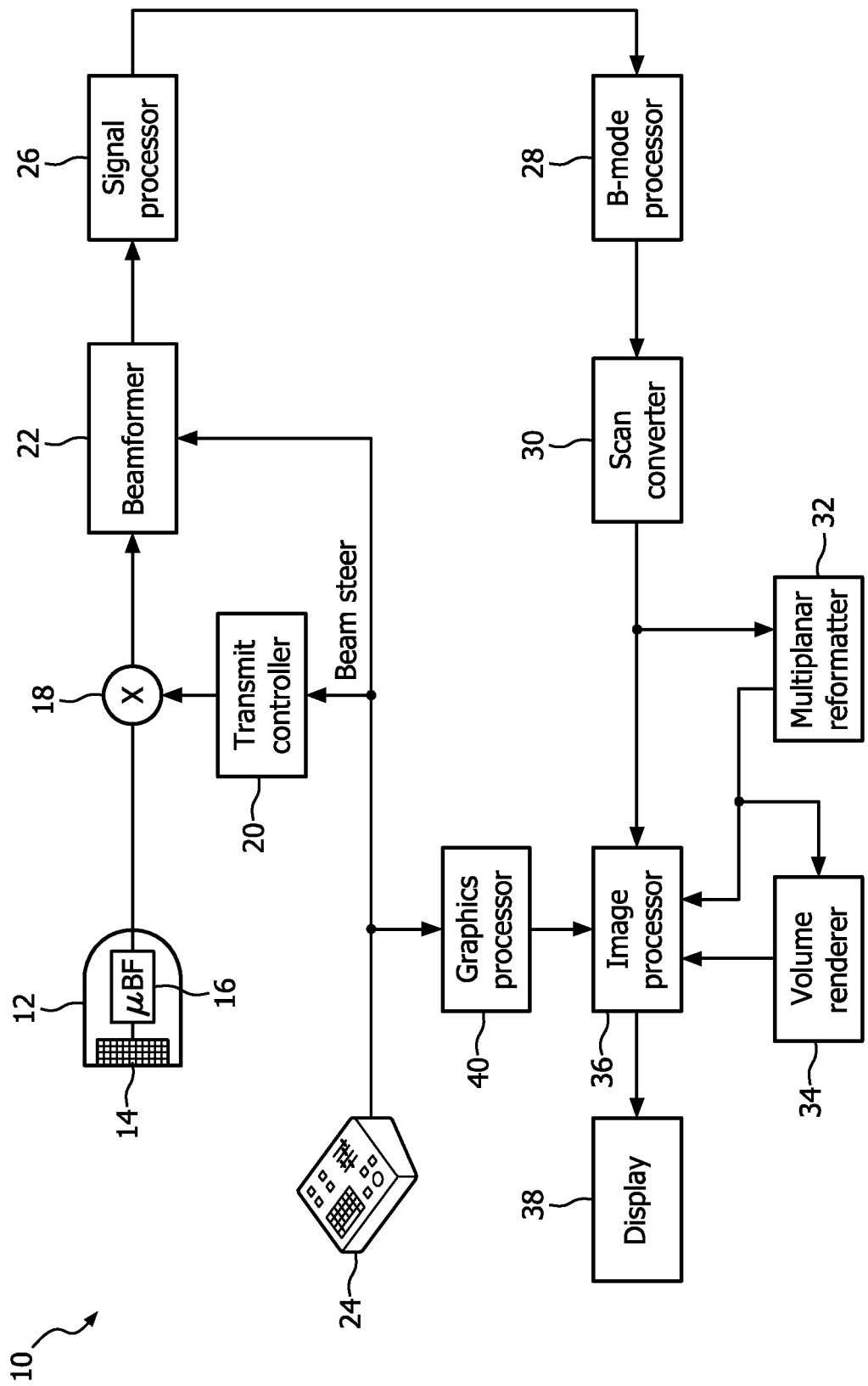
FIG. 1 is a block diagram of an imaging system according to embodiments of the present disclosure.

Referring now to FIG. 1, an ultrasound imaging system 10 constructed in accordance with the principles of the present invention is shown in block diagram form. Although an ultrasound imaging system is shown in explanatory examples of embodiments of the invention, embodiments of the invention may be practiced with other medical imaging modalities. Other modalities may include, but are not limited to, magnetic resonance imaging and computed tomography. In the ultrasound imaging system of FIG. 1, an ultrasound probe 12 includes a transducer array 14 for transmitting ultrasonic waves and receiving echo information. A variety of transducer arrays are well known in the art, e.g., linear arrays, convex arrays or phased arrays. The transducer array 14, for example, can include a two dimensional array (as shown) of transducer elements capable of scanning in both elevation and azimuth dimensions for 2D and/or 3D imaging. The transducer array 14 is coupled to a microbeamformer 16 in the probe 12 which controls transmission and reception of signals by the transducer elements in the array. In this example, the microbeamformer is coupled by the probe cable to a transmit/receive (T/R) switch 18, which switches between transmission and reception and protects the main beamformer 22 from high energy transmit signals. In some embodiments, the T/R switch 18 and other elements in the system can be included in the transducer probe rather than in a separate ultrasound system base. The transmission of ultrasonic beams from the transducer array 14 under control of the microbeamformer 16 is directed by the transmit controller 20 coupled to the T/R switch 18 and the beamformer 22, which receive input from the user's operation of the user interface or control panel 24. One of the functions controlled by the transmit controller 20 is the direction in which beams are steered. Beams may be steered straight ahead from (orthogonal to) the transducer array, or at different angles for a wider field of view. The partially beamformed signals produced by the microbeamformer 16 are coupled to a main beamformer 22 where partially beamformed signals from individual patches of transducer elements are combined into a fully beamformed signal.

The beamformed signals are coupled to a signal processor 26. The signal processor 26 can process the received echo signals in various ways, such as bandpass filtering, decimation, I and Q component separation, and harmonic signal separation. The signal processor 26 may also perform additional signal enhancement such as speckle reduction, signal compounding, and noise elimination. The processed signals are coupled to a B-mode processor 28, which can employ amplitude detection for the imaging of structures in the body. The signals produced by the B-mode processor are coupled to a scan converter 30 and a multiplanar reformatter 32. The scan converter 30 arranges the echo signals in the spatial relationship from which they were received in a desired image format. For instance, the scan converter 30 may arrange the echo signal into a two dimensional (2D) sector-shaped format, or a pyramidal three dimensional (3D) image. The multiplanar reformatter 32 can convert echoes which are received from points in a common plane in a volumetric region of the body into an ultrasonic image of that plane, as described in U.S. Pat. No. 6,443,896 (Detmer). A volume renderer 34 converts the echo signals of a 3D data set into a projected 3D image as viewed from a given reference point, e.g., as described in U.S. Pat. No. 6,530,885 (Entrekin et al.) The 2D or 3D images are coupled from the scan converter 30, multiplanar reformatter 32, and volume renderer 34 to an image processor 36 for further enhancement, buffering and temporary storage for display on an image display 38. The graphics processor 40 can generate graphic overlays for display with the ultrasound images. These graphic overlays can contain, e.g., standard identifying information such as patient name, date and time of the image, imaging parameters, and the like. For these purposes the graphics processor receives input from the user interface 24, such as a typed patient name. The user interface can also be coupled to the multiplanar reformatter 32 for selection and control of a display of multiple multiplanar reformatted (MPR) images.

Figure 2:
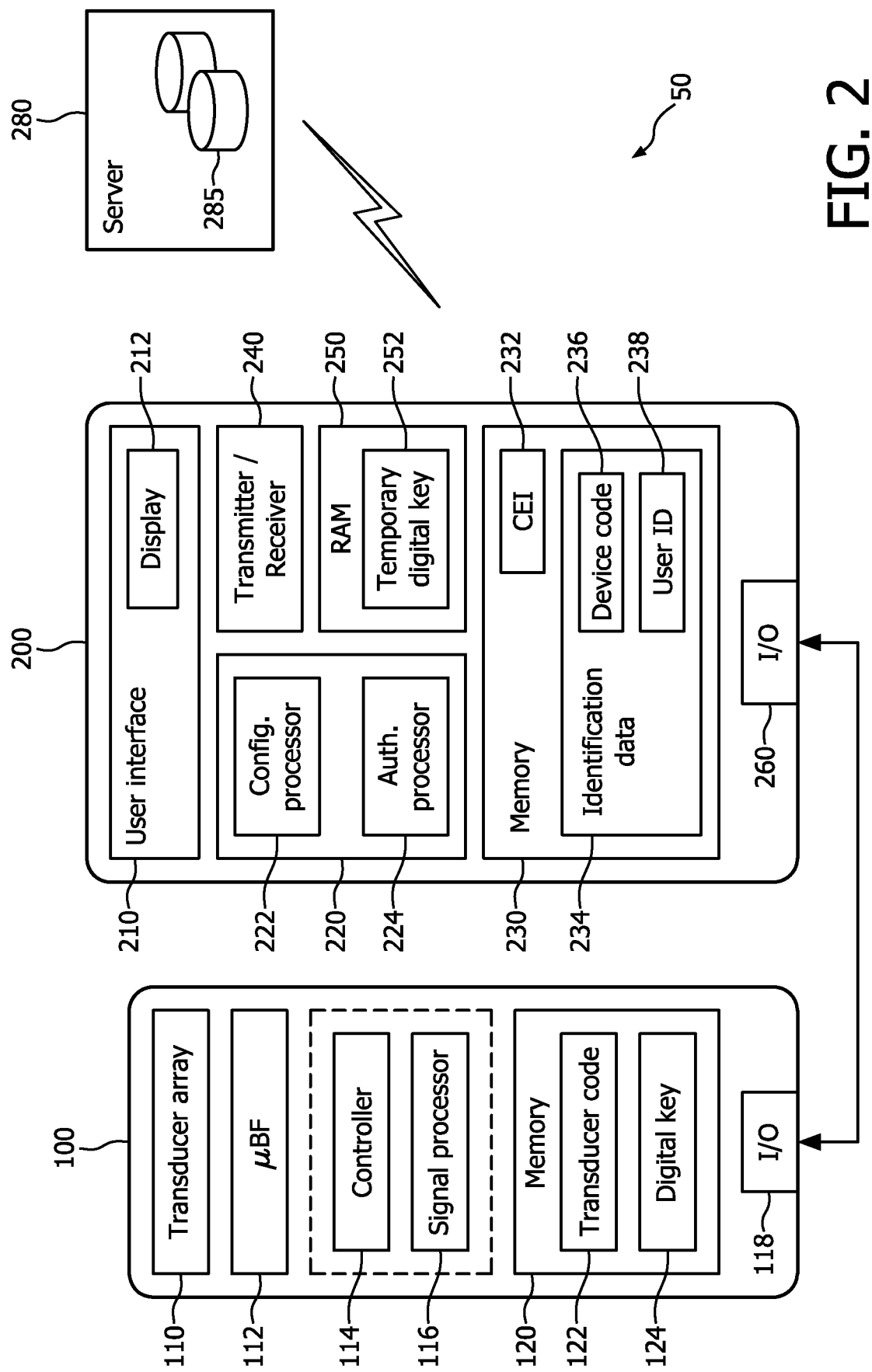
FIG. 2 is a block diagram of an operational environment including an imaging system according to embodiments of the present disclosure.

FIG. 2 illustrates an operational environment for a medical imaging system (e.g., an ultrasound imaging system) according to some embodiments of the present invention. In the operational environment 50, a transducer probe 100 may be removably coupled to an imaging device 200. The imaging device 200 is configured to perform medical imaging operations, such as ultrasound imaging. Although a single transducer probe and a single imaging device are illustrated in FIG. 2, it will be appreciated that any number of transducer probes and/or imaging devices may be involved in typical operational environment, such as operational environment 50.

The transducer probe 100 may include one or more of the components of the ultrasound imaging system described with reference to FIG. 1. For example, the transducer probe 100 may include a transducer array 110, a microbeamformer 112, and a controller 114. The controller 114 may be configured to control, among other things, the transmission and reception of signals to and from the array 110 and microbeamformer 112. The transmission and reception of signals to and from the array 110 and microbeamformer 112 may be performed under the direction of input from a user's operation of a user interface 210 of the imaging device 200. The user interface 210 may include any known or later developed user interface devices such as a keyboard, a cursor controller, a graphics display, and/or a touch display. In some examples, certain control inputs may be provided via controls (not shown) on the transducer probe 100.

Beamformed signals acquired with the transducer probe 100 may be processed by a signal processor 116 to obtain an image (e.g., ultrasonic image). Certain processing operations may be performed by a processor onboard the transducer probe (e.g., signal processor 116), a processor of the imaging device (e.g., processor 220), or a combination thereof. In some examples, functionality of the controller 114 and signal processor 116 may be combined within a single processing unit. The transducer probe 100 includes memory 120, which may store information generated during and/or used by the imaging device 200 in performing some of the processes described herein. For example, the memory 120 may store configuration data (e.g., FPGA configuration information) for configuration and/or operation of the transducer array 110. The memory 120 may store information associated with authentication features of the transducer probe 100, for example a transducer identification code 122 and one or more digital keys 124, as will be further described. The memory 120 may be any type of non-volatile memory, such as flash memory. The transducer probe 100 may also include one or more input/output devices 118 for connecting the transducer probe 100 to the imaging device. An example input/output device is a universal serial bus (USB) port. In some examples, the connection between the transducer probe and imaging device may be wireless. In some examples, the input/output devices 118 of the transducer probe may include a wireless communication circuit configured to establish a wireless connection with a wireless communication circuit on the imaging device.

The imaging device 200 may include one or more of the components of the imaging system 10 in FIG. 1. For example, the imaging device 200 may include a display 212 for displaying medical images thereon. In some examples, the display may be part of the user interface 210. In some examples, the display 212 may be configured to both provide output to the user and receive user inputs (e.g., a touch screen).

The imaging device 200 is configured to transmit and receive signals to and from the transducer probe 100 for displaying images acquired with the transducer probe 100. The imaging device 200 may include one or more processors. The imaging device 200 may include a graphics processor which is configured to generate graphic overlays for display with the ultrasound images. These graphic overlays can contain, for example identifying information such as patient name, date and time of the image, imaging parameters, and the like. The imaging device 200 may include a probe configuration processor 222 configured to perform functions for associating a transducer probe (e.g., transducer probe 100) with the imaging device 200, as described further below. The imaging device 200 may include a probe authentication processor 224 configured to perform functions for verifying an association between the imaging device 200 and a transducer probe (e.g., transducer probe 100). Any of the graphics processor, probe configuration processor 222, and the probe authentication processor 224 may receive input from the user interface 210. The functionality of one or more of the processors of imaging device 200 may be implemented in one or more separate integrated circuits or they may be integrated into a single processor (e.g., processor 220).

In some examples, the functionality of one or more of the processors of imaging device 200 may be implemented in software, which when executed by processor 220 program the imaging device 200 to perform the functions described herein. For example, the imaging device 200 may include computer executable instructions 232 for an imaging application which may be stored in memory (e.g., memory 230). The computer executable instructions 232 may include instructions for controlling imaging operations with the transducer probe 100. The computer executable instructions 232 may include instructions for configuring and/or authenticating the transducer probe for use with the imaging device 200.

In one embodiment, the imaging system 200 may be implemented in a portable computing device, such as a tablet, which includes a touch display, one or more memory devices, and one or more processors. The imaging system 200 in the form of a portable computing device may be coupled to a transducer probe (e.g. transducer probe 100) having a relatively small form factor. The transducer probe may perform substantially all of the functions necessary to produce a medical image and transmit video signals corresponding to the medical image to the imaging system 200. The memory of imaging system 200 may store computer executable instructions for performing the functions described herein. For example, the imaging system 200 may include computer executable instructions which when executed program the imaging system 200 to perform the functions of the probe configuration processor 222 and the probe authentication processor 224, as described herein, as well as functions associated with controlling the transducer probe 100 and displaying the video signals (e.g., image data) received from the transducer probe 100.

As described herein, the imaging device 200 may include one or more memory devices, such as memory 230, which may be non-volatile memory, and memory 250 which may be volatile memory (e.g., RAM 250). In addition to computer executable instructions, memory 230, may store certain identification data such as a unique device identification code 236 of the imaging device 200 and a unique user identification code, such as user identification number 238, of a user associated with the imaging device 200. The user identification code and device identification code may collectively be referred to as identification information. In some examples, the imaging device 200 is configured to generate temporary authentication information (e.g., temporary digital key 252) as will be described. In some example, such temporary authentication information may be stored in only in volatile memory 250 and deleted upon the occurrence of an event.

The imaging device 200 is wirelessly connected, at least during certain operations described herein, to a remote server 280. In this regard, the imaging device 200 may include one or more wireless communication devices, for example a WiFi enabled transmitter/receiver 240. In some examples, the imaging device 200 is programmed to execute a web browser application (also referred to as web portal) for connecting to the remote server 280. The web portal is configured to establish a secure wireless connection between imaging device 200 and the remote server 280. The remote server 280 includes one or more storage devices 285 which store identification information as described further below. The server 280 is configured to receive requests from imaging devices (e.g., imaging device 200), retrieve and/or generate identification information, and store the identification information for enabling the security processes described herein.

The imaging device may include one or more input/output devices 260. I/O device 260 of the imaging device 200 may be used for connecting the transducer probe 100 to the imaging device 200. An example I/O device is a universal serial bus (USB) port. In some examples, the connection between the transducer probe and imaging device may be wireless. In some examples, the I/O devices 260 of the imaging device may include a wireless communication circuit configured to establish a wireless connection with the transducer probe. In some examples, the transmitter/receiver 240 may provide the functionality of the I/O device 260.

Some or all of the components, functions or processes described above with reference to FIG. 2 may be implemented in the imaging system illustrated in FIG. 1. For example, the ultrasound probe 12 may include a memory device which stores information associated with authentication features of the probe, for example a probe identification code and one or more a digital keys, as described herein. Similar to the imaging system in FIG. 2, the imaging system 10 may include a probe configuration processor, a probe authentication processor, or combinations thereof. Any of the processors of the imaging system 10 (e.g., the configuration processor, the probe authentication processor, the signal processor, the b-mode processor, the image processor, and the graphics processor) may be integrated into a single chip configured to perform the functions described herein.

Referring now also to FIGS. 3-7, operations of an imaging system in accordance with embodiments of the present disclosure are described. According to some examples, a transducer probe (e.g., transducer probe 100) is connected, through wired or wireless connection, to an imaging device (e.g., imaging device 200). The imaging device is configured to perform imaging operations using the transducer probe. The imaging device is configured to perform functions for associating the transducer probe with a particular user and/or with one or more imaging devices. The imaging device is further configured to verifying an association of the transducer probe. In some examples, the imaging device is configured to execute an application such as an imaging application. In further examples, the imaging device is configured to execute a web portal application for exchanging information with a remote server (e.g., server 280). In some examples, the imaging system is configured such that at least some of the information (e.g., user identification number 238, transducer identification code 122, and imaging device identification code 236) for use in associating the transducer probe 100 with a user and/or the imaging device 200 may be available only through a connection with the server 280. In such examples, during a configuration process, a secure connection to the server 280 (e.g., through a web portal) may be established to obtain the information needed to generate a digital key. Some or all of the functionality for associating the transducer probe with a user and/or an imaging device may alternatively or additionally be performed on the server side, e.g., via the web portal application. In some examples, the sever 280 may be configured to execute the web portal application for generating the digital key, e.g., upon request from the imaging device 200. In some examples, the server 200 may include a configuration processor similar to the configuration processor 222 described herein, which may include functionality for associating a transducer probe (e.g., transducer probe 100) with a user and/or one or more imaging devices in accordance with the present disclosure.

A user session of the imaging application may be initiated responsive to user inputs prior to connecting the transducer probe to the imaging device. In some examples, connecting the transducer probe to the imaging device, e.g. by plugging the transducer cable into an I/O port of the imaging device, causes an imaging application to automatically execute. Prior to performing imaging operations, one or more initialization operations may be performed by the imaging device. For example, the imaging device may perform operations for validating system requirements to ensure that the transducer probe connected to imaging device may be properly operated with the particular imaging device to which the transducer has been connected. The system requirements may correspond to minimum system capability for producing images having at least a minimum image quality as may be set by a regulating body. Parameters such as power demand and image processing capability of the imaging device may be verified.

Figure 3:
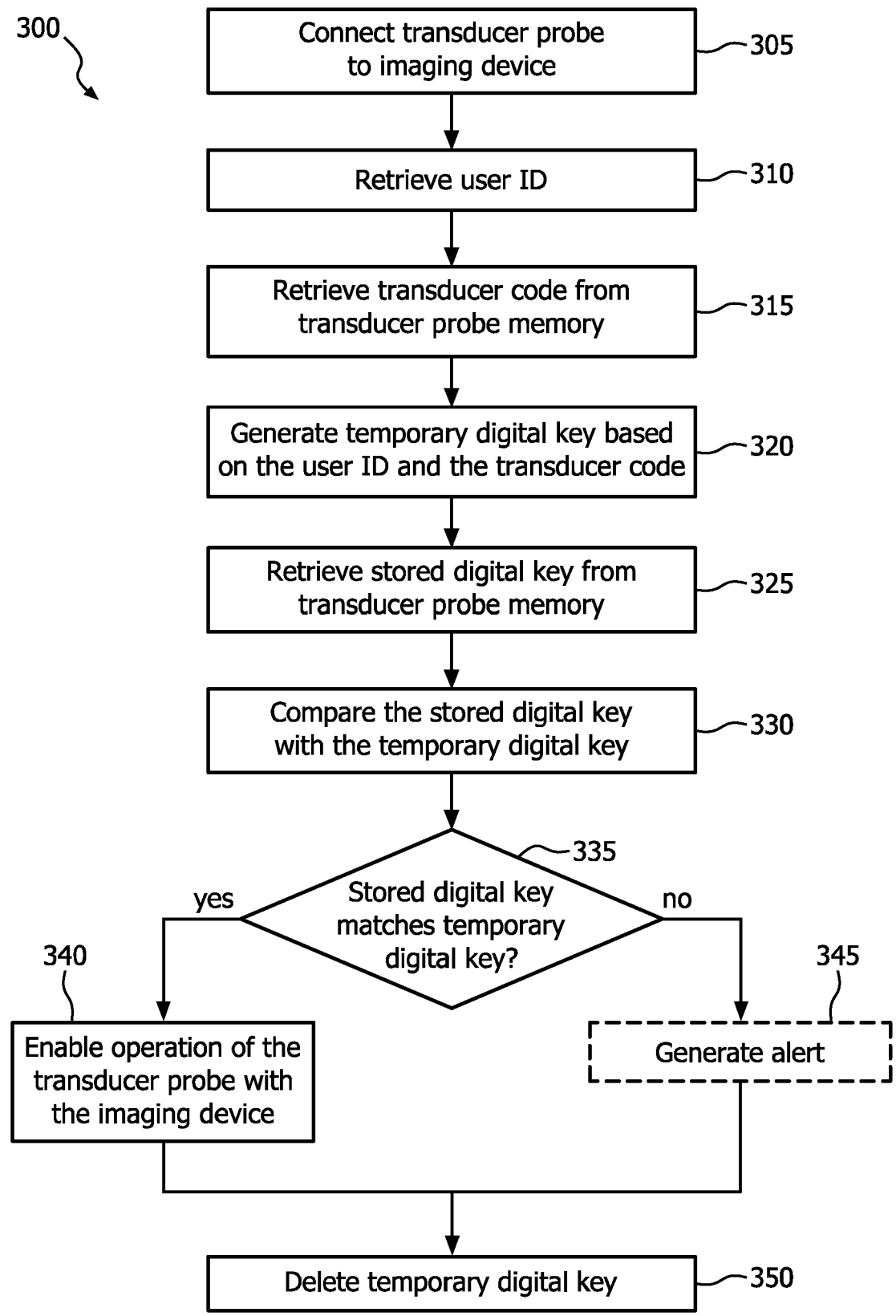
FIG. 3 is a flow diagram of a verification process according to some embodiments of the present disclosure.

The imaging device may be configured to verify an association of a transducer probe prior to enabling operation of the transducer probe with the imaging device. FIG. 3 illustrates an example verification process 300 (interchangeably referred to as authentication process) according to the present disclosure. With reference also to FIG. 2, the verification process 300 may be implemented in the probe authentication processor 224 of imaging device 200. The verification process 300 may include the steps of retrieving a user identification code, such as a user identification number, as shown in block 310, and retrieving a transducer identification code 122, as shown in block 315. The transducer identification code 122 may be a unique identifier associated with a particular transducer probe 100 or a class of transducer probes. Typically, the transducer identification code 122 is retrieved from the memory 120 of the transducer probe 100. In some examples, e.g., to simplify the manufacturing process and/or expedite delivery of a transducer probe to a customer, the transducer probe 100 may be shipped from the manufacturer without a transducer identification code programmed thereon. In such examples, the transducer identification code 122 is retrieved from the remote server 280 and subsequently stored in the memory 120 of the transducer probe 100, e.g., during a configuration process as will be described further below with reference to FIG. 4. The server 280 may be maintained by the manufacturer or a third party contracted by the manufacturer.

During the verification process 300, the user identification code, such as the user identification number 238, is typically retrieved from the memory 230 of the imaging device 200. The user identification number 238 may be a unique ID assigned to a user associated with the imaging device 200. For example, the user identification code may be a customer ID assigned, e.g., by the manufacturer of the imaging device to the purchaser of the imaging device. The terms customer and user may thus be used interchangeably herein. Customer IDs may be stored in a database maintained by the manufacturer, e.g., in the storage device 285 of server 280, and may be provided to a requesting imaging device during a configuration process, as will be described further with reference to FIG. 4.

Continuing with the example verification process 300, the process may further include the steps of generating a temporary digital key (block 320) and retrieving a stored digital key 124 from the transducer probe (block 325). The temporary digital key 252 is generated by the imaging device 200 after a connection to a transducer probe is detected by the imaging device 200. The temporary digital key 252 in this example is based on the user identification code and the transducer identification code 122 and is used by the imaging device 200 to verify that the particular transducer probe connected thereto is authorized for use with the imaging device. The stored digital key 124 is retrieved from the memory 120 of the transducer probe 100. The digital key 124 may be generated by the imaging device 200 and stored onboard the transducer probe 100 during a previous process, e.g., the configuration process illustrated in FIG. 4.

The association of the transducer probe 100 is verified by comparing the stored digital key 124 with the temporary digital key 252 as shown in block 330. If the stored digital key 124 retrieved from the memory 120 of the transducer probe 100 matches the temporary digital key 252 generated by the imaging device 200, e.g., as shown at block 335, operation of the transducer probe 100 with the imaging device 200 is enabled, as shown at block 340. In some examples, the process 300 optionally generates an alert (block 345), if the stored digital key 124 does not match the temporary digital key 252. The alert may be displayed on display 212 of the imaging device 200, stored in memory 230 of the imaging device 200, and/or transmitted to the remote server 280.

One or more of the steps of process 300 may occur automatically in response to connecting the transducer probe 100 to the imaging device 200 (as shown in block 305). The imaging device 200 may detect a connection, wired or wireless, with the transducer probe 100 and automatically perform one or more of the steps of process 300. By automatically, it is generally meant that a step is performed without requiring user input to initiate the step. In other examples, user inputs may be received via the user interface 210 to direct the imaging device 200 to perform one or more of the steps described herein. The transducer probe 100 may be connected to the imaging device 200 by plugging a transducer cable to an I/O port 118 (e.g., USB port) of the transducer probe 100 and an I/O port 260 (e.g., a USB port) of the imaging device 200. In the context of this disclosure, a USB port is understood to include any type of universal serial bus interface including without limitation interfaces configured for standard, mini, and micro USB type connectors. In some examples, a connection may be established between the transducer probe 100 and imaging device 200 via wireless communication between wireless communication circuits on the transducer probe 100 and imaging device 200.

In some examples, the temporary digital key 252 generated by imaging device 200 is temporarily buffered for use during the verification process and is subsequently automatically deleted following the verification steps described above. That is, in some examples, temporary digital key 252 is stored only in volatile memory (e.g., RAM 250) of imaging device 200 and is deleted at the end of the verification process, as shown in block 350. A new temporary digital key 252 is generated each time a new connection with a transducer probe is detected. In some examples, the temporary digital key 252 remains in memory 250 until an event occurs. In some examples, the event may correspond to the completion of the verification process. In some examples, the event may correspond to the transducer probe 100 being disconnected form the imaging device 200, terminating the execution of an imaging application on the imaging device 200, or powering down of the imaging device 200.

Figure 4:
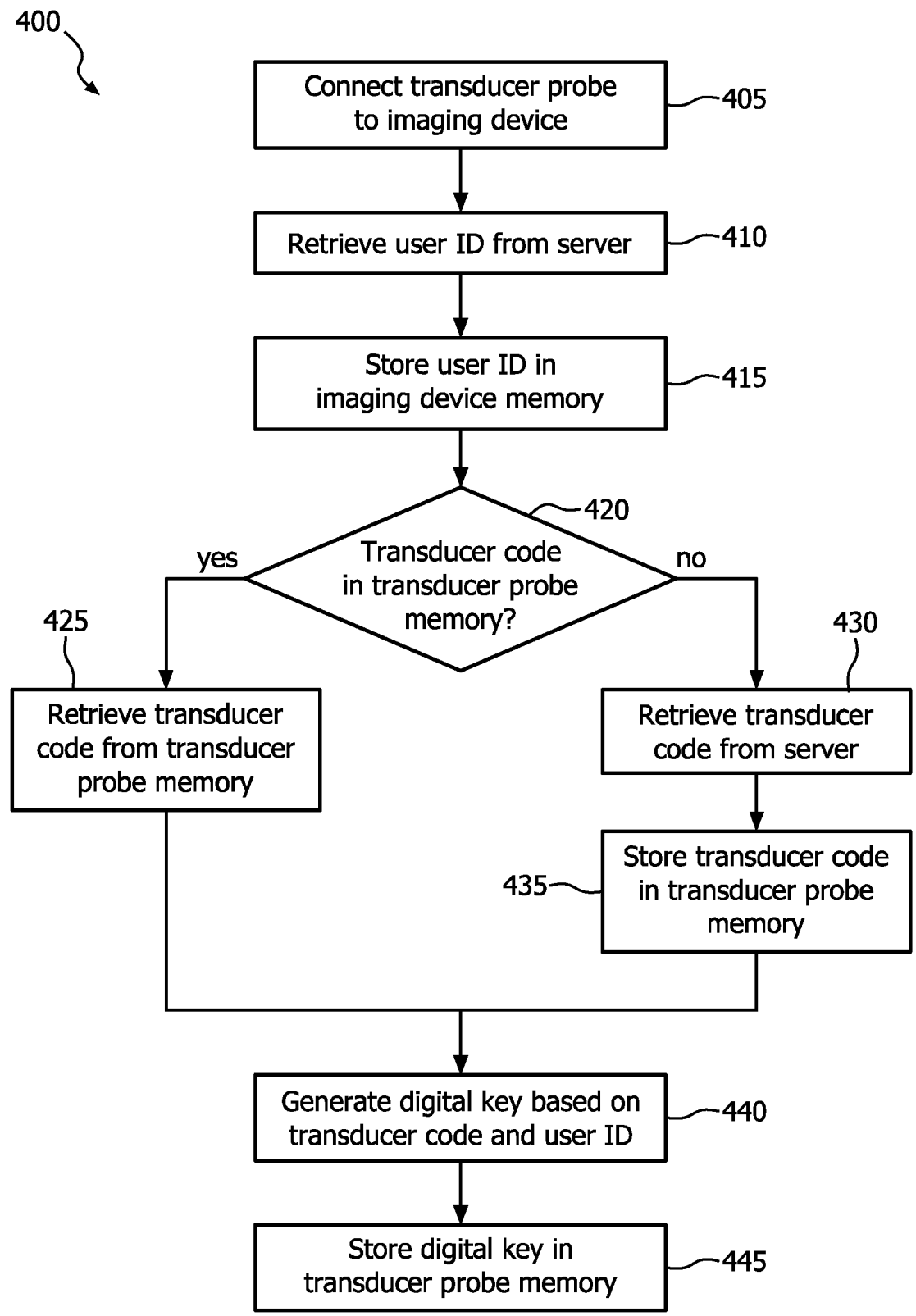
FIG. 4 is a flow diagram of a configuration process according to some embodiments of the present disclosure.

In some examples, the imaging device 200 is further configured to perform steps for associating a transducer probe for use with the imaging device. FIG. 4 illustrates an example configuration process 400 according to the present disclosure. The configuration process 400 may be implemented in the probe configuration processor 222 of the imaging device. The configuration process 400 may include the steps of retrieving the user identification code from a remote server 280 wirelessly coupled to the imaging device 200, as shown in block 405, and storing the user identification code in the memory 230 of the imaging device 200, as shown in block 415. The imaging device 200 may determine whether a transducer identification code 122 is stored in the memory 120 of the transducer probe 100, as shown in block 420 and if so, retrieve the transducer identification code 122 from the memory 120, as shown in block 425. Otherwise, a transducer identification code 122 is retrieved from the remote server 280, as shown in block 430, and stored in the memory 120 of the transducer probe 100, as shown in block 435. One or more of the steps of process 400 may occur automatically in response to connecting the transducer probe 100 to the imaging device 200, as shown in block 405. In other examples, user inputs may be received via the user interface 210 to direct the imaging device 200 to perform the steps described herein.

The example configuration process 400 may continue with the imaging device 200 generating a digital key 124, which is then stored in the memory 120 of the transducer probe 100. In some examples, the digital key 124 generated by imaging device 200 is temporarily buffered until it is transmitted to the transducer probe 100 and is subsequently automatically deleted following the configuration process. That is, in some examples, digital key 124 is stored only in volatile memory (e.g., RAM 250) of imaging device 200 and is deleted upon the occurrence of an event. In such examples, the digital key 124 remains in memory 250 until the event occurs. In some examples, the event may correspond to the completion of the configuration process. In some examples, the event may correspond to the transducer probe 100 being disconnected form the imaging device 200, terminating the execution of an imaging application on the imaging device 200, or powering down of the imaging device 200.

The digital key 124 in the example in FIG. 4 is a type 1 digital key, which is based on the user identification code 238 and the transducer identification code 122. In further examples, the digital key 124 may be based on additional identification information, such as the imaging device identification code as will be described further below with reference to FIG. 6.

As will be appreciated, during the configuration process 400, a unique digital key 124 may be generated and stored onboard the transducer probe 100 which associates the transducer probe 100 with one or more imaging devices that are associated with a particular user. Referring now also to FIG. 5 association of an exemplary number of transducers with an exemplary number of imaging devices is described.

The stored digital key 124-a of transducer 1, which in this example is based on a first transducer code and a first user id, associates the first transducer probe (transducer 1) with all of imaging devices that may be associated with a first user (user 1), in this example, imaging devices 1 through 4. Thus, when the transducer probe 100 is connected to any imaging device associated with the first user (e.g., any of the imaging devices 1 through 4), operation of the first transducer probe (transducer 1) will be enabled following a verification process (e.g., process 300) in which a temporary digital key generated by the imaging device and based on the first user id and the first transducer code, is matched to the stored digital key 124-a, which is also based on the first user id and first transducer code. In this manner, the stored digital key on the first transducer probe authenticates the first transducer probe for use with any of one or more imaging devices that are associated with the first user. The digital key 124-a in this example is referred to as a type 1 key. A type 1 key associates a transducer probe with all imaging devices that are associated with a given user.

If the first transducer probe (transducer 1) is instead connected to another imaging device that is not associated with the first user but is instead associated with a second user (e.g., imaging device 5), the stored digital key 124-a on the first transducer probe will not match the temporary digital key generated by the imaging device associated with the second user (e.g., imaging device 5) and operation of the first transducer probe with the second imaging device will not be enabled. As further illustrated in FIG. 5, a second transducer probe (transducer 2) may be registered and thereby associated with a second user that owns imaging device 5. A second user identification code is assigned, for example by the manufacturer of the imaging device and/or transducer probe, to the second user. During a configuration process (e.g., process 400), transducer 2 is connected to imaging device 5 and a digital key 124-b is generated by imaging device 5 based on the second user identification code and the transducer identification code of transducer 2 and stored on transducer 2. As indicated in the table in FIG. 5, transducer 2 is only associated with imaging devices associated with user 1, in this example imaging device 5 and is not associated with imaging devices of other users. Thus during normal operations, transducer 2 may be authenticated for use with imaging device 5 but not with imaging devices 1 through 4. The digital key 124-b, which is based on the transducer identification code and the user identification code, is a type 1 key similar to key 124-a described above.

In some cases, it may be desirable to limit the association of a transducer probe to a subset of imaging devices from the group of all imaging devices associated with a given user. In some examples, such as in a hospital or university setting, a customer may own and thus be associated with a large number of imaging devices. The customer may wish to authorize use of a particular transducer with only a subset of the imaging devices that the customer owns, e.g., for example imaging devices dedicated to a specific lab, practice group, or classroom. To that end, one or more digital keys based on further identifying information may be generated as described now with reference to FIG. 6.

Figure 6:
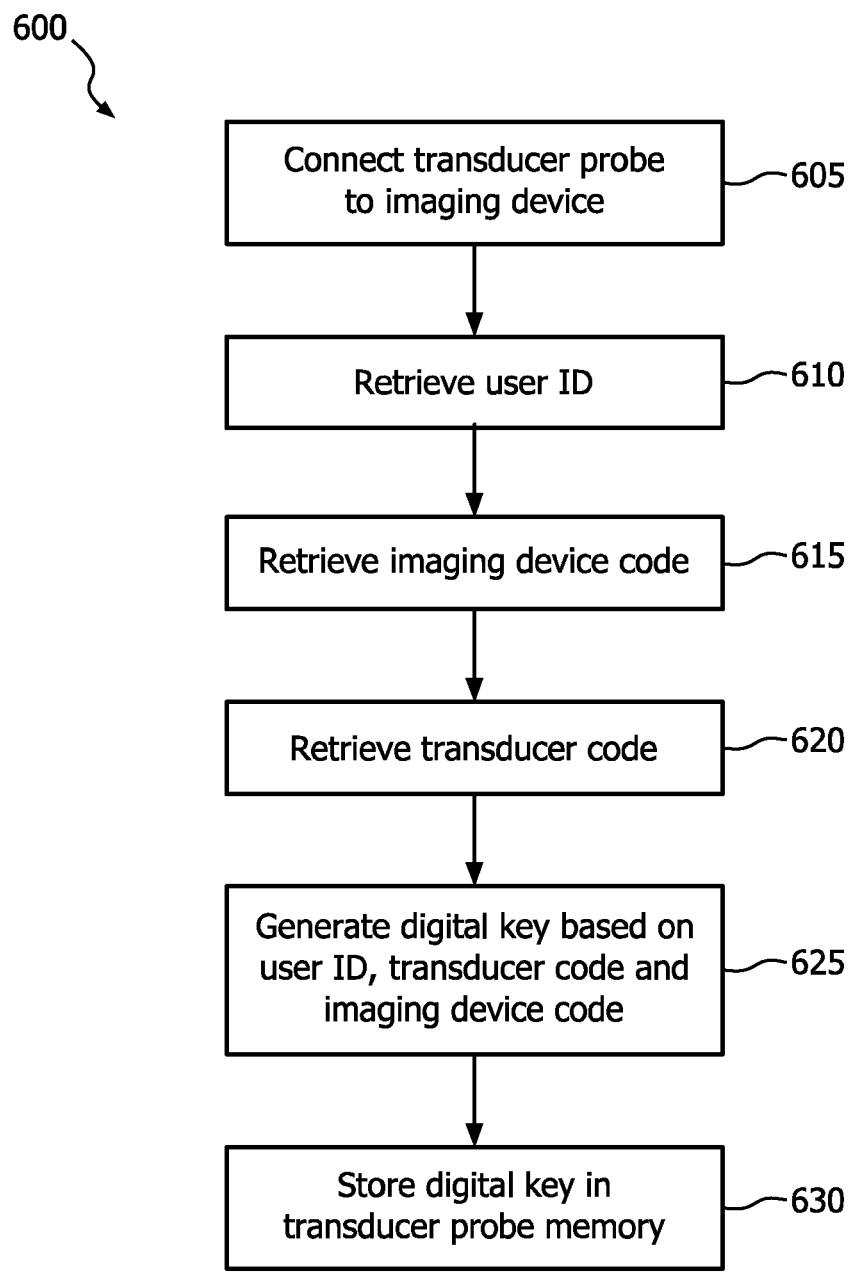
FIG. 6 is a flow diagram of a configuration process according to further embodiments of the present disclosure.
Figure 7:
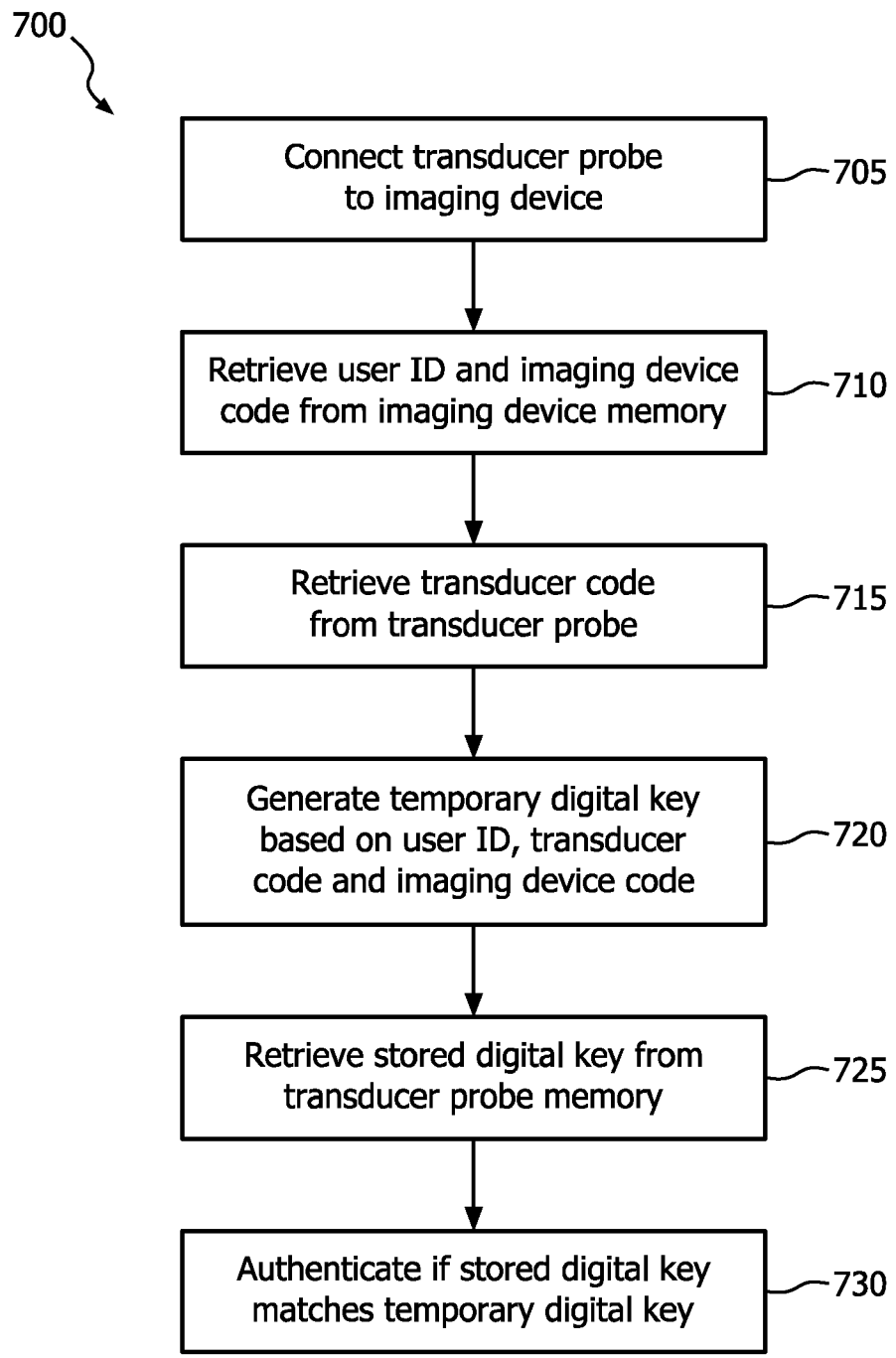
FIG. 7 is a flow diagram of a verification process according to further embodiments of the present disclosure.

FIG. 6 illustrates a configuration process 600 according to further example of the present disclosure. The configuration process 600 may be implemented in the probe configuration processor 222 of the imaging device. The configuration process 600 may include one or more of the steps of configuration process 400. The configuration process 600 may begin after a connection with a transducer probe 100 is detected by the imaging device 200, as shown in block 605. The process 600 may include the steps of retrieving a user identification number 238, an imaging device identification code 236, and a transducer identification code 122, as shown in blocks 610, 615, and 620, respectively. The imaging device identification code 236 may be a unique identifier of the imaging device 200, such as the serial number, which is typically programmed into the imaging device 200 by the manufacturer. In some examples, the imaging device identification code 236 may be an identifier of a class of imaging devices. The imaging device identification code 236 may be stored in a memory (e.g., memory 230) of the imaging device 200. The user identification number 238 may be stored in the memory 230 of the imaging device, e.g., as a result of a previously performed configuration process, or may alternatively be retrieved from the remote server 280. To that end, the imaging device 200 sends a request to the remote server 280 in which the imaging device 200 transmits the imaging device identification code 236 to server 280. The server 280 is configured to retrieve the user identification number 238 of the user associated with the particular imaging device 200 as identified using the imaging device's identification code 236. The server 280 returns the user identification number 238, which is then stored in the memory 230 of imaging device 200.

As described previously with reference to process 400, the transducer identification code 122 is typically stored in memory onboard the transducer probe and thus, the transducer identification code 122 is typically retrieved from the memory of the transducer probe 100. In some examples, the transducer identification code 122 may be obtained and stored in accordance with steps 420-435 of process 400. Thus, it will be understood, that process 600, optionally includes steps similar to steps 420-435 of process 400. In some examples, to retrieve the transducer identification code 122, the imaging device 200 sends a request to the server 280 in which the imaging device transmits to the server 280 the user identification number 238, the imaging device identification code 236, or both. The server 280 is configured to generate or retrieve the transducer identification code 122 based on the identification information provided by the imaging device 200. The server 280 returns the transducer identification number 122, which is then stored in the memory of imaging device 200.

Continuing with process 600, the imaging device 200 generates a digital key 124 based on the unique user identification number 238, transducer identification code 122, and imaging device identification code 236, as show in block 625. The digital key 124 is transmitted to the transducer probe 100, e.g., via a wired connection between the imaging device 200 and the transducer probe 100, and stored in the memory 120 of the transducer probe 100, as show in block 630.

The digital key 124 in the example in FIG. 6 is a type 2 key, which enables a limited association between a transducer probe and a subset of imaging devices from a larger group of imaging devices associated with a given user. Referring back to FIG. 5, transducer 3 includes a plurality of stored digital keys 124-*c*, 124-*d* which are type 2 keys. The digital key 124-*c* may be based on the user identification code of user 1, the transducer identification code of transducer 2, and the imaging device identification code of imaging device 1, thus enabling authentication of transducer 3 with imaging device 1. The digital key 124-*d* may be based on the user identification code of user 1, the transducer identification code of transducer 2, and the imaging device identification code of imaging device 2, thus further enabling authentication of transducer 2 with imaging device 2. As will be appreciated, the specific number of imaging devices, transducer probes, users and digital keys illustrated in FIG. 5 are provided only to enable the reader to understand the present disclosure and do not limit in any way the number of imaging devices, transducer probes, users and digital keys that may be included in embodiments in accordance with the present disclosure.

FIG. 6 illustrates a verification process 700 according to further example of the present disclosure. In the process 700, a transducer probe (e.g., transducer probe 100) is authenticated using a type 2 key. The verification process 700 may be implemented in the probe authentication processor 224 of the imaging device 200. The verification process 700 may include one or more of the steps of verification process 300. The verification process 700 may begin after a connection with a transducer probe 100 is detected by the imaging device 200, as shown in block 705. At block 710, the imaging device identification code 236 and the user identification number 238 of a user associated with the imaging device 200 are retrieved. The imaging device identification code 236 and the user identification number 238 may be retrieved from memory 230 of the imaging device 200. At block 715, the transducer identification code 122 of transducer probe 100 is retrieved, e.g., from memory 120 of the transducer probe 100. At block 720, the imaging device 200 generates a type 2 temporary digital key 252 based on the user identification number 234, the imaging device identification code 238, and the transducer identification code 122. The imaging device 200 retrieves a stored digital key 124 from the transducer probe 100 and compares the stored digital key 124 to the temporary digital key 252. Operation of the transducer probe 100 with imaging device 200 is enabled if the stored digital key 124 matches the temporary digital key 252. Similar to process 300, an alert may be generated if the stored digital key 124 does not match the temporary digital key 252. The alert may be displayed, stored and/or transmitted to server 280. In examples in which the transducer probe 100 stores a plurality of digital keys 124, the imaging device 200 parses through the stored digital keys 124 to identify a stored digital key that matches the temporary digital key 252. If a matching stored digital key is not found in the memory of transducer probe 100, the process terminates without enabling operation of the transducer probe 100 with imaging device 200.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", Pascal", "VHDL" and the like.

Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein.

For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system.

Certain additional advantages and features of this invention may be apparent to those skilled in the art upon studying the disclosure, or may be experienced by persons employing the novel system and method of the present invention, chief of which is that a more reliable image acquisition system and method of operation thereof is provided. Another advantage of the present systems and method is that conventional medical image systems can be easily upgraded to incorporate the features and advantages of the present systems, devices, and methods.

Of course, it is to be appreciated that any one of the above embodiments or processes may be combined with one or more other embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. A processor-readable storage medium including processor executable instructions, which when executed cause a medical imaging system to:
   retrieve, from a server, a user identification code assigned to a user associated with a computing device;
   store the user identification code in a memory of the computing device;
   retrieve, from a transducer probe, a transducer identification code of the transducer probe from a memory of the transducer probe;
   generate a digital key, based at least in part, on the user identification code and the transducer identification code:
   store the digital key in the memory of the transducer probe, thereby creating a stored digital key;
   generate a temporary digital key based on the user identification code and the transducer identification code, wherein the temporary digital key associates the user with the transducer probe;
   retrieve the stored digital key from the memory of the transducer probe;
   verify an association of the transducer probe with the computing device by comparing the stored digital key with the temporary digital key; and
   enable operation of the transducer probe with the computing device if, based on the comparison, the stored digital key matches the temporary digital key.

2. The storage medium of claim 1 further comprising instructions to delete the temporary digital key from the computing device following the verifying step.

3. The storage medium of claim 1 further comprising instructions to delete the temporary digital key from the computing device when the transducer probe is disconnected form the computing device, when the computing device is powered down, or when execution of an imaging application on the computing device is terminated.

4. The storage medium of claim 1 further comprising instructions to generate an alert if the temporary digital key does not match the stored digital key.

5. The storage medium of claim 1, wherein the instructions to associate the transducer probe with the computing device further comprise instructions to:
   transmit a request for the transducer identification code to the server;
   receive the transducer identification code from the server; and transmit the transducer identification code to the transducer probe to be stored in the memory of the transducer probe.

6. The storage medium of claim 1, wherein the instructions to associate the transducer probe with the computing device further comprise instructions to:
   transmit a request for the user identification code to the server, the transmitting a request for the user identification code including transmitting a device identification code to the server; retrieve the user identification code from the server; and store the user identification code in a memory of the computing device.

7. The storage medium of claim 1, wherein the instructions to associate the transducer probe with the computing device further comprise instructions to:
   retrieve a device identification code associated of the computing device from the memory of the computing device; and
   generate the digital key based further on the device identification code retrieved from the memory of the computing device.

8. The storage medium of claim 1 further comprising instructions to store the digital key, the temporary digital key, or both, only in volatile memory of the computing device.

9. A medical imaging system comprising:
   a computing device configured to be removably connected to a transducer probe, the computing device comprising:
   a memory configured to store a user identification code; and one or more processors including a probe authentication processor coupled to the memory, the probe authentication processor configured to:
   retrieve a user identification code from the computing device;
   retrieve a transducer identification code from the transducer probe;
   generate a digital key based, at least in part, on the transducer identification code and the user identification code;
   store the digital key in the transducer probe, thereby creating a stored digital key;
   generate a temporary digital key based, in part, on the user identification code and the transducer identification code, wherein the temporary digital key associates the user with the transducer probe;
   verify an association of the transducer probe with the computing device by comparing the stored digital key with the temporary digital key; and
   enable operation of the transducer probe with the computing device if, based on the comparison, the stored digital key matches the temporary digital key.

10. The system of claim 9, wherein the computing device is configured to delete the temporary digital key upon the occurrence of an event.

11. The system of claim 9, wherein the probe configuration processor is configured to generate the digital key based further on a device identification code of the computing device.

12. The system of claim 9, wherein the computing device is further configured to store the temporary digital key, the digital key, or both, only in volatile memory of the computing device.

13. The system of claim 9, wherein the computing device is further configured to generate an alert if the temporary digital key does not match the stored digital key.

14. The system of claim 9, further comprising the transducer probe, the transducer probe comprising a USB connector for coupling the transducer probe to the computing device.

15. The system of claim 9, further comprising the transducer probe, the memory of the transducer probe comprising a first stored digital key based on the user identification code, the transducer identification code, and a first computing device identification code, the transducer probe further comprising a second stored digital key based on the user identification code, the transducer identification code, and a second computing device identification code.

16. The system of claim 9, further comprising a server, the computing device wirelessly connected to the server, wherein the computing device is further configured to retrieve the user identification code from the server and store the user identification code in the memory of the computing device.

17. The system of claim 9, further comprising a server, the computing device wirelessly connected to the server, wherein the computing device is further configured to retrieve the transducer identification code from the server and transmit the transducer identification code to the transducer probe to be stored in a memory of the transducer probe.

18. The system of claim 15, wherein the probe authentication processor is configured to:
  compare the temporary digital key with the first stored digital key; responsive to determining that temporary digital key does not match the first stored digital key, compare the temporary digital key with the second stored digital key; and
  responsive to determining the temporary digital key matches the second stored digital key, enable operation of the transducer probe with the computing device.

* * * * *